United States Patent [19]

Byskov et al.

[11] Patent Number: 5,716,777
[45] Date of Patent: Feb. 10, 1998

[54] REGULATION OF MEIOSIS USING STEROLS

[75] Inventors: Anne Grete Byskov, Gentofte; Claus Yding Andersen, Copenhagen Ø; Lars Nordholm, Herlev; Henning Thøgersen, Farum; Ole Wassmann, Vallensbak; Ivan Verner Diers, Værløse; Erling Guddal, Brøndby, all of Denmark

[73] Assignee: Novo Nordisk A/S, Bagsvaerd, Denmark

[21] Appl. No.: 448,217

[22] Filed: May 23, 1995

[30] Foreign Application Priority Data

Jun. 23, 1994 [DK] Denmark .......................... 0753/94
Mar. 9, 1995 [DK] Denmark .......................... 0241/95

[51] Int. Cl.$^6$ .............. A01N 45/00; A01N 1/02; A61B 17/43
[52] U.S. Cl. .................. 435/2; 514/169; 600/33
[58] Field of Search ................. 435/2; 514/169; 600/33

[56] References Cited

PUBLICATIONS

Gunasekera et al., STN International, Medline Accession No. 90039331 (Abstract).

Bouvier et al., STN Internatinal, CAPLUS Accession No. 1977:85804 (Abstract).

Hansbury et al., STN International, HCAPLUS Accession No. 1981:26895 (Abstract).

Crosby et al., STN International, HCAPLUS Accession No. 1969:439215 (Abstract).

Pierce et al., STN International, HCAPLUS Accession No. 1978:500829 (Abstract).

Raederstorff et al., STN International, HCAPLUS Accession No. 1987:436317 (Abstract).

Byskov et al., Chemical Abstract, vol. 122., No. 19, 1995.

Dolle et al., J. Am. Chem. Soc., vol. 111, pp. 278–284, 1989.

Byskov et al., Nature, vol. 374, pp. 559–562, 1995.

*Primary Examiner*—Sandra E. Saucier
*Attorney, Agent, or Firm*—Steve T. Zelson, Esq.; Valeta Gregg, Esq.

[57] ABSTRACT

The present invention relates to certain sterol derivatives for use as medicaments.

5 Claims, No Drawings

REGULATION OF MEIOSIS USING STEROLS

FIELD OF THE INVENTION

The present invention relates to certain sterol derivatives for use as medicaments. More particularly it has been found that certain sterol derivatives can be used for regulating the meiosis.

BACKGROUND OF THE INVENTION

Meiosis is the unique and ultimate event of germ cells on which sexual reproduction is based. Meiosis comprises two meiotic divisions. During the first division, exchange between maternal and paternal genes take place before the pairs of chromosomes are separated into the two daughter cells. These contain only half the number (1 n) of chromosomes and 2 c DNA. The second meiotic division proceeds without a DNA synthesis. This division therefore results in the formation of the haploid germ cells with only 1 c DNA.

The meiotic events are similar in the male and female germ cells, but the time schedule and the differentiation processes which lead to ova and to spermatozoa differ profoundly. All female germ cells enter the prophase of the first meiotic division early in life, often before birth, but all are arrested as oocytes later in the prophase (dictyate state) until ovulation after puberty. Thus, from early life the female has a stock of oocytes which is drawn upon until the stock is exhausted. Meiosis in females is not completed until after fertilization, and results in only one ovum and two abortive polar bodies per germ cell. In contrast, only some of the male germ cells enter meiosis from puberty and leave a stem population of germ cells throughout life. Once initiated, meiosis in the male cell proceeds without significant delay and produces 4 spermatozoa.

Only little is known about the mechanisms which control the initiation of meiosis in the male and in the female. In the oocyte, new studies indicate that follicular purines, hypoxanthine or adenosine, could be responsible for meiotic arrest (Downs et al., *Der. Biol.* 82, pp. 454–58 (1985); Eppig et al., *Dev. Biol.* 119, pp. 313–21 (1986); and Downs, *Mol. Reprod. Dev.* 35, pp. 82–94 (1993)). The presence of a diffusible meiosis regulating substances were first described by Byskov et al. in a culture system of fetal mouse gonads (Byskov et al., *Dev. Biol.* 52, pp. 193–200 (1976)). A meiosis inducing substance (MIS) was secreted by the fetal mouse ovary in which meiosis was ongoing, and a meiosis preventing substance (MPS) was released from the morphologically differentiated testis with resting, non-meiotic germ cells. It was suggested that the relative concentrations of MIS and MPS regulated the beginning, arrest and resumption of meiosis in the male and in the femme germ cells (Byskov et al. in The Physiology of Reproduction (eds. Knobil and Neill, Raven Press, New York (1994)). Clearly, if meiosis can be regulated, reproduction can be controlled. Unfortunately, up till now it has not been possible to identify a meiosis inducing substance.

SUMMARY OF THE INVENTION

It has surprisingly been found that certain steroids known as intermediates in the biosynthesis of cholesterol and some novel, structurally related synthetic steroids can be used for regulating the meiosis.

Accordingly, the present invention relates to a compound of formula (I)

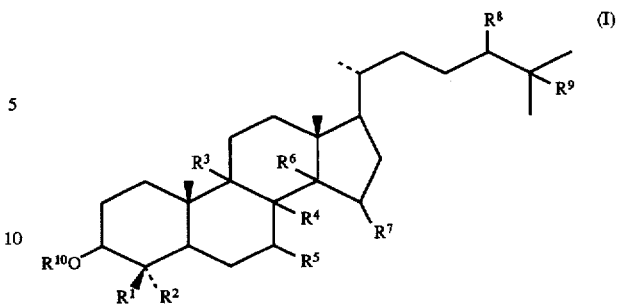

wherein $R^1$ and $R^2$, independently, are selected from the group comprising hydrogen, unbranched or branched $C_1$–$C_6$ alkyl which may be substituted by halogen or hydroxy or wherein $R^1$ and $R^2$ together with the carbon atom to which they are bound form a cyclopentane ring or a cyclohexane ring;

$R^3$ and $R^4$ together designate an additional bond between the carbon atoms to which they are bound in which case $R^5$ is hydrogen and $R^6$ and $R^7$ are either hydrogen or together they designate an additional double bond between the carbon atoms to which they are bound; or $R^5$ and $R^4$ together designate an additional bond between the carbon atoms to which they are bound in which case $R^3$ is hydrogen and $R^6$ and $R^7$ are either hydrogen or together they designate an additional bond between the carbon atoms to which they are bound; or $R^6$ and $R^4$ together designate an additional bond between the carbon atoms to which they are bound in which case $R^3$, $R^5$ and $R^7$ are all hydrogen;

$R^8$ and $R^9$ are hydrogen or together they designate an additional bond between the carbon atoms to which they are bound; and $R^{10}$ is either hydrogen or an acyl group or a group which together with the remaining part of the molecule forms an ether, for use as a medicament.

In a further aspect, the present invention relates to novel compounds of formula (I).

In the present context, the expression "regulating the meiosis" is understood to indicate that the compounds can be used for stimulating the meiosis in vitro, in vivo, and ex vivo.

Accordingly, in a more specific aspect, the present invention relates to the use of a compound of formula (I) above in the regulation of the meiosis.

In a still further aspect, the present invention relates to a method of regulating the meiosis in a mammalian germ cell which method comprises administering an effective mount of a compound of formula (I) above to a germ cell in need of such a treatment.

DETAILED DESCRIPTION OF THE INVENTION

It has been found, that the meiosis inducing substances extracted from bull testes and from human follicular fluid are both able to induce resumption of meiosis in cultured mouse oocytes (the oocyte test) and also to stimulate the meiosis in male germ cells of cultured fetal mouse testes (the gonad test). A meiosis inducing substance is produced by adult testes of various mammals, including man, and is also found in mature ovarian follicles of several mammalian species, including women. As it appears from the Examples 1 and 2, the meiosis inducing substance found in bull testes is 4,4-dimethylzymosterol while the meiosis inducing substance found in human follicular fluid is 4,4-dimethyl-5α-cholesta-8,14,24-triene-3β-ol.

The existence of a meiosis inducing substances has been known for some time. However, until now the identity of the meiosis inducing substance or substances has been unknown. To the best of the knowledge of the present inventors, no practical use of the compounds of formula (I) has so far been made in medicine. In particular, no compounds of formula (I) have so far been used as medicaments for regulating the meiosis.

The prospects of being able to influence the meiosis are several. According to a preferred embodiment of the present invention, the compounds of formula (I) are used to stimulate the meiosis. According to another preferred embodiment of the present invention, the compounds of formula (I) are used to stimulate the meiosis in humans. Thus, the compounds of formula (I) are promising as new fertility regulating agents without the usual side effect on the somatic cells which are known from the hitherto used hormonal contraceptives which are based on estrogens and/or gestagens. For use as a contraceptive agent in females, a meiosis inducing substance can be administered so as to prematurely induce resumption of meiosis in oocytes while they are still in the growing follicle, before the ovulatory peak of gonadotropins occurs. In women, the resumption of the meiosis can, for example, be induced a week after the preceding menstruation has ceased. When ovulated, the resulting overmature oocytes are most likely not to be fertilized. The normal menstrual cycle is not likely to be affected. In this connection it is important to notice, that the progesterone synthesis in cultured human granulosa cells (somatic cells of the follicle) is not affected by the presence of a meiosis inducing substance whereas the estrogens and gestagens used in the hitherto used hormonal contraceptives do have an adverse effect on the progesterone synthesis.

According to another aspect of this invention, a meiosis inducing substance of formula (I) can be used in the treatment of certain cases of infertility in females, including women, by administration thereof to females who, due to an insufficient own production of MIS, are unable to produce mature oocytes. Also, when in vitro fertilization is performed, better results are achieved, when a meiosis inducing substance of formula (I) is added to the medium in which the oocytes are kept.

Also, when infertility in males, including men, is caused by an insufficient own production of the meiosis inducing substance administration of a meiosis inducing substance of formula (I) may relieve the problem.

The route of administration of the compositions containing a compound of formula (I) may be any route which effectively transports the active compound to its site of action.

Thus, when the compounds of this invention are to be administered to a mammal, they are conveniently provided in the form of a pharmaceutical composition which comprise at least one compound of formula (I) in connection with a pharmaceutically acceptable carrier. For oral use, such compositions are preferably in the form of capsules or tablets.

From the above it will be understood that administrative regimen called for will depend on the condition to be treated. Thus, when used in the treatment of infertility the administration may be once only, or for a limited period, e.g. until pregnancy is achieved. When used as a contraceptive, the meiosis inducing substance of formula (I) will either have to be taken continuously or cyclically. When used as a contraceptive by women and not taken continuously, the timing relative to the menstrual cycle will be important.

The pharmaceutical compositions may comprise carriers, diluents, absorption enhancers, preservatives, buffers, agents for adjusting the osmotic pressure, tablet disintegrating agents and other ingredients which are conventionally used in the art. Examples of solid carriers are magnesium carbonate, magnesium stearate, dextrin, lactose, sugar, talc, gelatin, pectin, tragacanth, methyl cellulose, sodium carboxymethyl cellulose, low melting waxes and cocoa butter.

Liquid compositions include sterile solutions, suspensions and emulsions. Such liquid compositions may be suitable for injection or for use in connection with ex vivo and in vitro fertilization. The liquid compositions may contain other ingredients which are conventionally used in the art, some of which are mentioned in the list above.

Further, a composition for transdermal administration of a compound of this invention may be provided in the form of a patch and a composition for nasal administration may be provided in the form of a nasal spray in liquid or powder form.

The dose of a compound of the invention to be used will be determined by a physician and will depend, inter alia, on the particular compound employed, on the route of administration and on the purpose of the use.

Preferred compounds of formula (I) are the following:
Cholest-7-ene-3β-ol;
4-Methylcholest-7-ene-3β-ol;
4-Ethylcholest-7-ene-3β-ol;
4,4-Dimethylcholest-7-ene-3β-ol;
4α-Methyl-4β-ethylcholest-7-ene-3β-ol;
4α-Ethyl-4β-methylcholest-7-ene-3β-ol;
4,4-Diethylcholest-7-ene-3β-ol;
4-Propylcholest-7-ene-3β-ol;
4-Butylcholest-7- ene-3β-ol;
4-Isobutylcholest-7-ene-3β-ol;
4,4-Tetramethylenecholest-7-ene-3β-ol;
4,4-Pentamethylenecholest-7-ene-3β-ol;
Cholest-8-ene-3β-ol;
4-Methylcholest-8-ene-3β-ol;
4-Ethylcholest-8-ene-3β-ol;
4,4-Dimethylcholest-8-ene-3β-ol;
4α-Methyl-4β-ethylcholest-8-ene-3β-ol;
4α-Ethyl-4β-methylcholest-8-ene-3β-ol;
4,4-Diethylcholest-8-ene-3β-ol;
4-Propylcholest-8-ene-3β-ol;
4-Butylcholest-8-ene-3β-ol;
4-Isobutylcholest-8-ene-3β-ol;
4,4-Tetramethylenecholest-8-ene-362 -ol;
4,4-Pentamethylenecholest-8-ene-3β-ol;
Cholest-8(14)-ene-3β-ol;
4-Methylcholest-8(14)-ene-3β-ol;
4-Ethylcholest-8(14)-ene-3β-ol;
4,4-Dimethylcholest-8(14)-ene-3-ol;
4α-Methyl-4β-ethylcholest-8(14)-ene-3β-ol;
6α-Ethyl-4β-methylcholest-8(14)-ene-3β-ol;
4,4-Diethylcholest-8(14)-ene-3β-ol;
4-Propylcholest-8(14)-ene-3β-ol;
4-Butylcholest-8(14)-ene-3β-ol;
4-Isobutylcholest-8(14)-ene-3β-ol;
4,4-Tetramethylenecholest-8(14)-ene-3β-ol;
4,4-Pentamethylenecholest-8(14)-ene-3β-ol;
Cholesta-8,14-diene-3β-ol;
4-Methylcholesta-8,14-diene-3β-ol;
4-Ethylcholesta-8,14-diene-3β-ol;
4,4-Dimethylcholesta-8,14-diene-3β-ol;
4α-Methyl-4β-ethylcholesta-8,14-diene-3β-ol;
4α-Ethyl-4β-methylcholesta-8,14-diene-3β-ol;
4,4-Diethylcholesta-8,14-diene-3β-ol;
4-Propylcholesta-8,14-diene-3β-ol;
4-Butylcholesta-8,14- diene-3β-ol;

4-Isobutylcholesta-8, 14-diene-3β-ol;
4,4-Tetramethylenecholesta-8,14-diene-3β-ol;
4,4-Pentamethylenecholesta-8,14-diene-3β-ol;
Cholesta-8,24-diene-3β-ol;
4-Methylcholesta-8,24-diene-3β-ol;
4-Ethylcholesta-8,24-diene-3β-ol;
4,4-Dimethylcholesta-8,24-diene-3β-ol;
4α-Methyl-4β-ethylcholesta-8,24-diene-3β-ol;
4α-Ethyl-4β-methylcholesta-8,24-diene-3β-ol;
4,4-Diethylcholesta-8,24-diene-3β-ol;
4-Propylcholesta-8,24-diene-3β-ol;
4-Butylcholesta-8,24-diene-3β-ol;
4-Isobutylcholesta-8,24-diene-3β-ol;
4,4-Tetramethylenecholesta-8,24-diene-3β-ol;
4,4-Pentamethylenecholesta-8,24-diene-3β-ol;
Cholesta-8,14,24-triene-3β-ol;
4-Methylcholesta-8,14,24-triene-3β-ol;
4-Ethylcholesta-8,14,24-triene-3β-ol;
4,4-Dimethylcholesta-8,14,24-triene-3β-ol;
4α-Methyl-4β-ethylcholesta-8,14,24-triene-3β-ol;
4α-Ethyl-4β-methylcholesta-8,14,24-triene-3β-ol;
4,4-Diethylcholesta-8,14,24-triene-3β-ol;
4-Propylcholesta-8,14,24-triene-3β-ol;
4-Butylcholesta-8,14,24-triene-3β-ol;
4-Isobutylcholesta-8,14,24-triene-3β-ol;
4,4-Tetramethylenecholesta-8,14,24-triene-3β-ol; and
4,4-Pentamethylenecholesta-8,14,24-triene-3β-ol;
and esters and ethers thereof.

Preferred esters of formula (I) are those in which $R^{10}$ is acetyl, benzoyl, pivaloyl, butyryl, nicotinoyl, isordcotinoyl, hemi succinoyl, hemi glutaroyl, butylcarbamoyl, phenylcarbamoyl, butoxycarbonyl, tert-butoxycarbonyl or ethoxycarbonyl.

Preferred ethers of formula (I) are those wherein $R^{10}$ is a methoxymethyl group or a pivaloyloxymethyl group.

The naturally occurring compounds according to the present invention can be obtained from natural sources by methods known per se. Alternatively, they may—like the structurally related synthetic sterols of the present invention—be obtained by synthesis by methods known per se.

The present invention is further illustrated by the following examples which, however, are not to be construed as limiting the scope of protection. The features disclosed in the foregoing description and in the following examples may, both separately and in any combination thereof, be material for realizing the invention in diverse forms thereof.

EXAMPLES

Example 1

Isolation, purification and identification of a meiosis inducing substance (MIS) from bull testes.

Testes from a six years old bull (Danish Landrace) were removed immediately after slaughter. The tunica albuginea was removed and the testicular tissue placed on dry ice and stored at −80° C. Frozen testicular tissue (92 g) was minced into pieces smaller than 1 mm³ and freeze dried in the dark until completely dry, approximately 90 h. The freeze dried tissue was extracted with 400 ml of n-heptane (LiChrosolv, Merck 4390, Germany) under nitrogen with stirring for 24 h at 20° C. The suspension was filtered and the solid material was extracted once more following the same procedure. The pooled organic phases were evaporated to dryness on a rotatory evaporator at room temperature yielding 981 mg of extracted material. This material was dissolved in n-heptane and portioned into 15 vials from which the n-heptane was evaporated. The vials were stored under nitrogen at 4° C. in the dark.

A three-step HPLC purification was employed for the extracts:

In the first step, the content of one vial was dissolved in 50 μl of 50% (v/v) tetrahydrofuran (THF) in water and applied to the reversed phase HPLC column (LiChroSpher 100 RP-8 endcapped 5 μm, 250×4 mm i.d., Merck). The elution was performed at 40° C. using a linear gradient of THF going from 50% to 100% in 15 min (flow: 1 ml/min). 18 fractions of 1 ml were collected and tested for MIS-activity.

In the second step, fractions from the first step which were found active in the oocyte-assay were dissolved in 50–100 μl of 70% THF and applied to a column similar to the one used in the first step. The elution was performed at 40° C. using a linear gradient of THF going from 60% to 78% in 16 min (flow: 1 ml/min). 8 fractions of 1 ml were collected and tested for MIS-activity.

In the third step, fractions from the second step which were found active in the oocyte-assay were dissolved in 100 μl of n-heptane:2-propanol (98:2) (v/v) and applied to a semipreparative HPLC column (ChromSpher Si 5 μm, 250× 10 mm i.d., Chrompack). The elution was performed at room temperature using a mobile phase consisting of n-heptane:2-propanol, 98:2 (v/v) (flow: 5 ml/min). Five fractions of 2.5 ml were collected and tested for MIS-activity.

In all three steps, the elution was monitored by UV-detection at 220 nm.

Material which had been through the three-step purification procedure described above was used to study the molecular structure of the active compound by nuclear magnetic resonance spectrometry (NMR) and by mass spectrometry.

For the NMR spectra, approximately 1 mg of purified material was dissolved in 0.6 ml of deuterochloroform A $^{13}$C proton decoupled NMR spectrum, a $^1$H NMR spectrum (with and without resolution enhancement) and a 2D TOCSY spectrum were recorded on a Bruker AMX2 400 NMR spectrometer equipped with an inverse broad band 5 mm probe head with gradient coil. The $^{13}$C-NMR chemical shifts in ppm (δ) for the isolated MIS are given in Table 1 for comparison with the corresponding data for zymosterol (Taylor et al., *J. Lipid Res.* 22, p. 171 (1981)) and lanosterol (Emmons et al. *Magn. Res. Chem.* 27, p. 1012 (1989)).

TABLE 1

| Carbon | Zymosterol | Lanosterol | MIS |
| --- | --- | --- | --- |
| 1 | 35.1 | 35.5 | 35.8 |
| 2 | 31.5 | 27.8 | 28.0 |
| 3 | 70.9 | 79.0 | 79.0 |
| 4 | 38.2 | 38.9 | 38.9 |
| 5 | 40.7 | 50.4 | 50.2 |
| 6 | 25.5 | 18.2 | 18.4 |
| 7 | 27.1 | 26.5 | 28.5 |
| 8 | 128.0 | 134.4 | 128.0 |
| 9 | 134.8 | 134.4 | 135.8 |
| 10 | 35.6 | 37.0 | 37.0 |
| 11 | 22.8 | 21.0 | 22.1 |
| 12 | 36.9 | 30.9 | 29.7 |
| 13 | 42.0 | 44.4 | 42.1 |
| 14 | 51.8 | 49.8 | 51.9 |
| 15 | 23.7 | 30.8 | 23.8 |
| 16 | 28.7 | 28.2 | 28.8 |
| 17 | 54.7 | 50.4 | 54.8 |
| 18 | 11.2 | 15.7 | 11.3 |
| 19 | 17.8 | 19.1 | 19.8 |
| 20 | 36.0 | 36.2 | 36.0 |
| 21 | 18.6 | 18.6 | 18.6 |

TABLE 1-continued

| Carbon | Zymosterol | Lanosterol | MIS |
|---|---|---|---|
| 22 | 36.0 | 36.3 | 36.1 |
| 23 | 24.7 | 24.9 | 24.8 |
| 24 | 125.0 | 125.2 | 125.2 |
| 25 | 130.6 | 130.9 | 130.9 |
| 26 | 17.6 | 17.6 | 17.6 |
| 27 | 25.7 | 25.7 | 25.7 |
| 28 |  | 15.4 | 15.4 |
| 29 |  | 27.9 | 27.9 |
| 30 |  | 24.2 |  |

Mass spectrometry was performed using a VG Trio 1000 LC/MS instrument with LINC particle beam interphase and LAB-BASE 2.1 software (Fisons Instruments) with a HPLC system comprising a ChromSpher Si, 3 µm, 100×4.6 mm column (Chrompack). The HPLC was performed at room temperature and n-heptane:2-propanol, 98:2 (v/v) was used as mobile phase (flow: 0.6 ml/min). The sample of the MIS to be injected was dissolved in n-heptane. The mass spectrometer was operated in electron impact mode. Results are given in Table 2 in which the relative peak heights for the isolated product is compared to data for 4,4-dimethylzymosterol from Ref. 1. Under Ref. 2 a "+" designates that the corresponding peak was also reported in this study. A "−" under Ref. 1 or 2 designates that the corresponding peak was not reported in these studies.

TABLE 2

| m/z | Interpretation | MIS | Ref. 1 | Ref. 2 |
|---|---|---|---|---|
| 412 | [M]$^+$ | 100 | 100 | + |
| 397 | [M—CH$_3$]$^+$ | 60 | 42 | + |
| 379 | [M—CH$_3$—H$_2$O]$^+$ | 24 | 17 | + |
| 301 | [M—SC]$^+$ | 11 | − | + |
| 299 | [M—SC—2H]$^+$ | 22 | 13 | − |
| 274 | [M—SC—C$_2$H$_3$]$^+$ | 8 | 8 | − |
| 259 | [M—SC—C$_3$H$_6$]$^+$ | 21 | 33 | + |
| 241 | [M—SC—C$_3$H$_6$—H$_2$O]$^+$ | 44 | 33 | + |

SC = side chain, C$_2$H$_3$ = position 16 and 17, C$_3$H$_6$ = position 15, 16 and 17.
Ref. 1: Baloch et al., Phytochemistry 23, p. 2219 (1984).
Ref. 2: Morimoto et al. Liebigs Ann. Chem. 708, p. 230 (1967).

Based on the $^{13}$C-NMR spectrum and its molecular weight of 412 as determined by mass spectroscopy (MS), the structure of the MIS isolated from bull testes was proposed to be 4,4-dimethyl-5α-choleste-8,24-diene-3β-ol, also designated 4,4-dimethylzymosterol (DMZ). The chemical shifts of the individual carbon atoms of the MIS-active material from the third HPLC purification step were compared with the chemical shifts of the structurally very closely related compounds lanosterol and zymosterol. The observed proton chemical shifts, coupling constants and TOCSY correlations fully support that the isolated compound is 4,4-dimethylzymosterol.

Example 2

Isolation, purification and identification of a meiosis inducing substance (MIS) from human follicular fluid.

Human follicular fluid (FF) was obtained from follicles aspirated for oocyte collection in the treatment of infertility by in vitro fertilization. The fluid was freeze dried and extracted with n-heptane and the extract was purified using the same procedures as described in Example 1. The compound of the active peak had a molecular ion of m/z=410 and the mass spectrum revealed that the chemical structure of the FF-MIS molecule is 4,4-dimethyl-5α-cholesta-8,14,24-triene-3β-ol.

Methods: Mass spectrometry was performed using a VG Trio 1000 LC/MS with LINC particle beam interphase and LAB-BASE 2.1 software (Fisons Instruments) connected to a straight phase HPLC system consisting of a ChromSpher Si, 3 µm, 100×4 mm i.d. column (Chrompack) and n-heptane:2-propanol:methanol:ammonia (68:30:2:0.2) as mobile phase (flow: 0.5 ml/min) at room temperature. The sample of the MIS to be injected was dissolved in n-heptane. The mass spectrometer was operated in electron impact mode. Results are shown in Table 3.

TABLE 3

| m/z | | Interpretation |
|---|---|---|
| 410 | = M | [M]$^+$ (Mw for FF-MIS) |
| 395 | M-15 | [M—CH$_3$]$^+$ |
| 392 | M-18 | [M—H$_2$O]$^+$ |
| 377 | M-33 | [M—CH$_3$—H$_2$O]$^+$ |
| 349 | M-61 | [M-43-H$_2$O]$^+$ |
| 381 | M-129 | [M—SC—H$_2$O]$^+$ (SC = 111) |
| 279 | M-131 | [M—SC—2H—H$_2$O]$^+$ |
| 257 | M-153 | [M—SC-42]$^+$ |
| 255 | M-155 | [M-154-H]$^+$ |
| 239 | M-171 | [M—SC-42-H$_2$O]$^+$ |

SC = side chain

Example 3

Preparation of 4β-methylzymosterol by fermentation.

Step A

The yeast strain Kluyveromyces bulgaricus A3410 was inoculated on a YPG agarslant and grown for 3 days at 30° C. in a thermostated incubator. 5 ml of sterile YE medium was added to the slant and the yeast colonies were suspended in the liquid medium by shaking of the robe on a whirlimixer. The suspension of cells was then dram up into a 5 ml sterile syringe and added to a 500 ml shakeflask with two baffle intrusions in the bottom. The flask contained 200 ml of ZYM medium. The flask was fixed on a rotating table and propagated for 24 hours at 250 rpm, 30° C. 0.4 ml of a sterile filtered amphotericin B solution was now added to the flask and the propagation was continued for further 25 hours. The yeast cells were harvested by centrifugation (Beckman model J6, 5° C., 10 min, 4000 rpm) and washed once in water. The cell slurry was isolated in a small plastic container and stored at −18° C. before the final extraction of the sterols.

The nutrient media and the amphotericin B solution mentioned above had the following composition:

YPG agar

| Yeast extract, Difco | 4 g |
|---|---|
| KH$_2$PO$_4$ | 1 g |
| MgSO$_4$.7H$_2$O | 0.5 g |
| Glucose | 15 g |
| Agar | 20 g |
| Deionized water | 1000 ml |
| pH adjusted to 5.8 before autoclaving at 121° C., 20 min. | |

YE medium

| yeast extract, Difco | 10 g |
|---|---|
| Deionized water | 1000 ml |
| Autoclaving 121° C., 20 min. | |

ZYM medium

| | |
|---|---|
| Yeast extract, Difco | 20 g |
| Peptone, Bacto | 10 g |
| Tap water | 1000 ml |
| pH adjusted to 6.5–6.6 before autoclaving 121° C., 20 min. | |
| Glucose (added separately after autoclaving) | 60 g |

Amphotericin B solution 1 mg of Fungizone® (Lyophilized cake of 50 mg amphotericin B, 41 mg sodium deoxycholate and 20.2 mg sodium phosphate from Squibb) dissolved in 1 ml deionized water.

Step B

The cultured cells from step A were suspended in 10 ml of water and 10 ml of 40% KOH in methanol were added. The mixture was heated to reflux for 4 hours, left overnight at room temperature, and then extracted twice with 20 ml of n-heptane. The combined extracts were washed with 10% sodium chloride solution and then with water until neutral (five times) and dried. Evaporation of the solvent left 40 mg of crude sterols.

Step C

The crude sterols from step B were dissolved in 1 ml of n-heptane/2-propanol (98:2) and shaken on a vortex mixer, centrifuged at 5000 rpm for 10 min and then subjected to HPLC:

Column: LiChroSorb DIOL 10 μm, 250×4 mm i.d. (Merck)
Eluent: n-heptane/2-propanol (98:2)
Flow: 1.1 ml/min, 20° C.
Detection: UV at 220 nm The peak eluting after 6.8 min was collected from several runs. The collected fractions were pooled and the solvent was evaporated to leave a residue which was submitted to mass spectrometry, and tested in the oocyte test.

The data of the mass spectrum which are reported in Table 4 are identical with those of 4β-methylzymosterol as recorded in the National Bureau of Standards library.

TABLE 4

| m/z | | Interpretation |
|---|---|---|
| 398 | = M | [M]$^+$ (Mw of 4β-methylzymosterol) |
| 383 | M-15 | [M—CH$_3$]$^+$ |
| 380 | M-18 | [M—H$_2$O]$^+$ |
| 365 | M-33 | [M—CH$_3$—H$_2$O]$^+$ |
| 269 | M-129 | [M—SC—H$_2$O]$^+$ (SC = 111) |
| 267 | M-131 | [M—SC—H$_2$O—2H]$^+$ |
| 245 | M-153 | [M—SC—C$_3$H$_6$]$^+$ |
| 227 | M-171 | [M—SC—C$_3$H$_6$—H$_2$O]$^+$ |
| 213 | M-185 | [M—SC—C$_4$H$_8$—H$_2$O]$^+$ |

SC = Side Chain

Example 4

Preparation of 4,4-dimethylcholesta-8,14-dien-3β-ol.

This compound was prepared as described by Schroepfer et al., Chemistry and Physics of Lipids 47, p. 187 (1988), and showed physical constants as described in the literature.

Example 5

Preparation of 4,4-dimethylcholest-8-ene-3β-ol.

Step A 2.48 g of 4,4-dimethylcholesta-8,14-diene-3-ol (Example 4) was dissolved in 20 ml of pyridine at 0° C. 1.7 g of benzoyl chloride was added, and the mixture was stirred at ambient temperature overnight. After evaporation to dryness, 25 ml of toluene was added and after standard aqueous workup, evaporation and trituration with acetone, 2.3 g (74%) of crystalline benzoate was obtained.

The $^1$H-NMR spectrum (CDCl$_3$, δ) showed characteristic signals at: 8.1 (d,2H); 7.55 (t,1H); 7.4 (t,2H); 5.4 (s,broad, 1H); 4.2 (dd,1H).

Step B 2.04 g of 3-benzoyloxy-4,4-dimethylcholesta-8,14-diene (Step A) was dissolved in 50 ml of THF, and 360 ml of 1M borane in THF was added dropwise at 0° C. The mixture was stirred at ambient temperature overnight, cooled to 0° C., and 140 ml of water was added dropwise, followed by 360 ml of 10% sodium hydroxide and 378 ml of 30% hydrogen peroxide. After stirring for 90 mutes, 100 ml of diethyl ether was added to the mixture and the aqueous phase extracted twice with diethyl ether. The combined organic phases were washed twice with sodium bisulphite solution and then with water. After evaporation, the product was purified by chromatography on SiO$_2$ (2% diethyl ether in toluene) to yield 0.62 g of 3-benzoyloxy-4,4-dimethylcholest-8-en-15-ol.

MS (molecular ion): 534.4.

The $^1$H-NMR spectrum (CDCl$_3$, δ) showed characteristic signals at: 8.0 (d,2H); 7.5 (t,1H); 7.4 (t,2H); 4.75 (m,1H); 4.1 (m,1H).

Step C 0.54 g of 3-benzoyloxy-4,4-dimethylcholest-8-en-15-ol was dissolved in 2.7 ml of pyridine at 0° C. and 33 mg of dimethylaminopyridine and 287 mg of phenylchlorothioformate was added cautiously. The mixture was stirred for 20 hours at ambient temperature. After addition of 25 ml of diethyl ether, the mixture was washed 6 times with a saturated solution of copper sulphate, water, twice with 10% sodium hydroxide, water and brine, and evaporated to yield 0.68 g of crude 3-benzoyl-4,4-dimethylcholest-8-ene-15-phenylthiocarbonate, which was farther processed by dissolving in 20 ml of toluene and treated with 370 mg of tributyltin hydride and 20 mg of azo-isobutyronitril. The mixture was heated at 90° C. for 20 minutes, and the same treatment was repeated. After evaporation, the mixture was roughly purified by chromatography on SiO$_2$ (heptane/methylene chloride: 70/30) to yield 150 mg of crude 3-benzoyloxy-4,4-dimethylcholest-8-ene, contaminated with the corresponding 8,14-diene (Step A).

Step D 150 mg of the mixture prepared in Step C was dissolved in 2 ml of methylene chloride, cooled to 0° C. 0.7 ml of diisobutylaluminiumhydride was added dropwise and after 15 minutes, 0.15 ml of water was added cautiously. Then, 25 ml of diethyl ether was added, and the organic phase was washed twice with a saturated solution of potassium sodium tartrate, with water and with brine, and evaporated to yield 130 mg of a mixture that was chromatographed on AgNO$_3$/SiO$_2$ (prepared as described in: Chem. & Phys. of Lipids 63, p. 115 (1992)) and eluted with toluene. Crystallization from ether/methanol yielded 49 mg of the title compound. Melting point: 154°–155° C. MS (molecular ion): 414.4.

The $^{13}$C-NMR spectrum (CDCl$_3$, 100.6 MHz) showed characteristic signals at 78.49 (C$_3$); 127.49 (C$_8$); 135.35 (C$_9$).

Example 6

Preparation of 3-Acetoxy-4,4-dimethylcholesta-8,14-diene.

1.3 g of 4,4-dimethylcholesta-8,14-diene-3-ol (Schroepfer et al., Chemistry and Physics of Lipids 47, p. 187 (1988)) were dissolved in 7.5 ml of pyridine and 7.5 ml of acetic anhydride and stirred at 22° C. overnight. The mixture was evaporated in vacuo, stripped twice with toluene, and purified by flash chromatography on SiO$_2$ (toluene). The first 300 ml of eluate was evaporated, and the product crystallized from diethyl ether to yield 140 mg of 3-acetoxy-8,14-dimethylcholestadiene. Melting point: 120°–125° C. (with destruction). MS (molecular ion): 454.4.

The $^1$H-NMR spectrum (CDCl$_3$, δ) showed characteristic signals at: 5.4 (s,broad,1H); 4.5 (dd,1H); 2.0 (s,3H):

Example 7

Preparation of cholesta- 8,14-diene-3β-ol.

770 mg of dehydrocholesterol was dissolved in a mixture of 2.7 ml of benzene, 19 ml of ethanol and 2.7 ml of concentrated hydrochloric acid and heated at reflux temperature for 3 hours. The mixture was cooled in an ice bath whereby a first crop of 110 mg of crystals were obtained. Evaporation of the filtrate to dryness and crystallization from ether/methanol gave a second crop of 220 mg of crystals, which was combined with the first crop and chromatographed on AgNO$_3$/SiO$_2$ (prepared as described in Example 5, step D) and eluted with 2.5% acetone in in toluene to yield 94 mg of pure cholesta-8,14-diene-3β-ol. Melting point: 113°–114.5° C. MS (molecular ion): 384.4.

The $^1$H-NMR spectrum (CDCl$_3$, δ) of the product showed characteristic signals at: 5.35 (s,broad,1H); 3.6 (m,1H).

The $^{13}$C-NMR spectrum (CDCl$_3$, 50.3 MHz) showed characteristic signals at: 70.99(C$_3$); 117.42(C$_{15}$); 123.1(C$_8$); 140.8(C$_9$); 151.1(C$_{14}$).

Example 8

Preparation of 4,4-tetramethylenecholesta-8,14-dien-3-ol.
Step A 1.15 g of dehydrocholesterol was dissolved in 15 ml of 2-butanone, 0.34 g of aluminum isopropoxide was added, and the mixture was heated at reflux temperature for 75 mutes. After cooling on an ice bath, 15 ml of 2N hydrochloric acid was added, the phases were separated, and the organic phase was washed twice with 7.5 ml of 2N hydrochloric acid. The aqueous phase was extracted with toluene, and the combined organic phases were washed with water and brine, dried, and evaporated to yield 1.18 g of crude cholesta-5,7-diene-3-one as a viscous oil.

The $^1$H-NMR spectrum showed characteristic signals at: 5.8(s,1H); 5.2(m,1H); 3.2(d,1H); 2.7(dd,1H).
Step B 0.67 g of potassium tert-butoxide was dissolved in 16 ml of tert-butanol at 45° C., 0.57 g of cholesta-5,7-diene-3-one was added, and the mixture was stirred for 10 mutes. 0.47 g of 1,4-diiodobutane was added, and the mixture was stirred for 30 minutes. The solvent was evaporated, the residue redissolved in toluene and water, and a little brine was added to induce separation of the phases. The organic phase was washed four times with water, and the combined aqueous phases were extracted once with toluene. The combined toluene extracts were dried and evaporated to yield 0.45 g of a foam, which after crystallization from diethyl ether/methanol yielded 0.35 g of crystalline 4,4-tetramethylenecholesta-5,7-diene-3-one. MS (molecular ion): 436.4.

The $^1$H-NMR spectrum (CDCl$_3$δ) showed characteristic signals at 5.75 (d,1H); 5.5(m,1H).
Step C 130 mg of LiAlH$_4$ was suspended in 6 ml of THF, and 1.97 g of 4,4-tetramethylenecholesta-5,7-diene-3-one dissolved in 40 ml of THF was added dropwise over 30 minutes. 15 minutes after the addition was completed there still remained some unreacted starting material (TLC), and an additional 65 mg of LiAlH$_4$ was added. After stirring for 30 minutes the reaction was complete, and 0.9 ml of water dissolved in 5 ml of THF was added dropwise. After 30 minutes stirring, excess of magnesium sulphate was added, and the mixture stirred for another 30 minutes, filtered and evaporated to dryness. The residue was dissolved in 25 ml of diethyl ether and 25 ml of methanol, and the ether was cautiously removed in vacuo. After stirring overnight, 1.75 g of crystalline 4,4-tetramethylene-cholesta-5,7-diene-3-ol was isolated by filtration. MS (molecular ion): 438.4.

The $^1$H-NMR spectrum showed characteristic signals at: 5.8(d,1H); 5.5(m,1H); 3.5(m,1H).
Step D 770 mg of the compound prepared in step C was dissolved in a mixture of 2.38 ml of benzene, 17.5 ml of ethanol, and 2.38 ml of concentrated hydrochloric acid and heated at reflux for 16 hours, and evaporated in vacuo. The residue was redissolved in 5 ml of toluene, filtered, and chromatographed on a medium pressure column of AgNO$_3$/SiO$_3$ (heptane:toluene, 10:90) to yield 35 mg of 4,4-tetramethylene-cholesta-8,14-diene-3-ol. MS (molecular ion): 438.4.

The $^1$H-NMR spectrum (CDCl$_3$, δ) showed characteristic signals at 5.35 (s,broad,1H); 3.3 (d,d,1H).

The $^{13}$C-NMR spectrum (CDCl$_3$,100.6 MHz) showed characteristic signals at: 79.0(C$_3$); 117.4(C$_{15}$); 122.9(C$_8$); 141.3(C$_9$); 151.1(C$_{14}$).

Example 9

Preparation of 4,4-Dimethylcholest-8(14)-ene-3β-ol.

580 mg of 4,4-dimethylcholest-8-ene-3β-ol was dissolved in 20 ml of diethyl ether and 20 ml of acetic acid. 60 mg of 10% Pd/C catalyst was added and the mixture was left with stirring overnight under hydrogen at 3.5 atm. The catalyst was removed, and the filtrate concentrated to 10 ml, whereby crystallization started. 10 ml of methanol was added, and the crystals were collected after 16 hours. Recrystallization from methanol yielded 230 mg of material, which was shown by $^1$H- and $^{13}$C-NMR to be a mixture of the 8(9) and 8(14)-isomers.

The mixture was redissolved in 10 ml of diethyl ether and 10 ml of acetic acid. 75 mg of 5% Pt/C catalyst was added, and the mixture treated with hydrogen overnight at atmospheric pressure. The catalyst was removed, the solvent evaporated, and the crystalline residue triturated with 5 ml of methanol to yield 190 mg of pure 4,4-dimethylcholest-8 (i4)-ene-3β-ol. MS (molecular ion): 414.4

$^{13}$C-NMR spectrum (CDCl$_3$, 100.6 MHz) shows characteristic signals at: 79.24(C$_3$); 126.1 l(C$_8$); 142.20(C$_{14}$).

Example 10

Test of meiosis inducing substances in the oocyte test.
Animals

Immature female mice (B6D2-F1, strain C57B1/2J) were kept under controlled fighting (14 hr light, 10 hr dark) and temperature, with food and water ad libitum. When the animals reached a weight of 13–16 grams (which correspond to the age of 20 to 22 days post partum) they were given a single injection (i.p.) of human menopausal gonadotropin (Humegon, Organon, The Netherlands) containing approximately 20 IU FSH and 20 IU LH (Ziebe et al., *Hum. Reprod.* 8, pp. 385–88 (1993)). 48 hours later the animals were killed by cervical dislocation.
Collection and culture of oocytes The ovaries were removed, placed in HX-medium (see below) and freed of extraneous tissue. The collection- and culture medium consisted of Eagles minimum essential medium (Flow, USA), containing 4 mM hypoxanthine, 3 mg/ml of bovine serum albumin, 0.23 mM sodium pyruvate, 2 mM glutamine, 100 U/ml of penicillin, and 100 µg/ml of streptomycin (all Sigma, USA). This medium is termed HX-medium. The same medium but without HX was used as control medium.

The antral follicles of the ovaries were punctured under a dissecting microscope using a 27-gauge needle. Cumulus enclosed oocyte (CEO) of uniform size were selected and rinsed three times in fresh HX-medium.

Oocytes freed from cumulus cells, i.e. denuded oocytes, DO, were obtained by gentle flushing CEO through a fine-bore mouth-controlled piper. CEO and DO were cultured in 4-well multidishes (Nunclon, Denmark) containing 0.5 ml of HX-medium except the controls which were cultured in control medium. Each well contained 35 to 50 oocytes. The test cultures were made with different concentrations of the compounds to be tested as indicated in Table 5.

The cultures were performed at 37° C. and 100% humidity with 5% $CO_2$ in air. The culture time was 24 hours.

Examination of oocytes

By the end of the culture period the number of oocytes with germinal vesicle (GV) or germinal vesicle breakdown (GVBD) and those with polar body (PB) was counted in an inverted microscope with differential interference contrast equipment. The percentage of oocytes with GVBD per total number of oocytes and the percentage of oocytes with PB per GVBD was calculated. The results for DO and CEO, calculated as units of MIS activity, are given in Table 5. One unit of MIS activity is defined as:

%GVBD$_{control}$/2 and the number of MIS activity units is calculated as:

2(%GVBD$_{test}$—%GVBD$_{control}$)/%GVBD$_{control}$

TABLE 5

| Substance | DO | CEO | Concentration, µg/ml |
|---|---|---|---|
| 4,4-Dimethyl- | 2.7 | 2.9 | 1.2 |
| zymosterol | 1.8 | 2.7 | 0.3 |
|  | 0.6 | 1.3 | 0.2 |
|  | 1.5 | 1.3 | 0.02 |
|  | 0.9 | 1.0 | 0.002 |
| 4,4-Dimethyl-5α-cholesta- | 0.6 | 2.3 | 0.3 |
| 8,14,24-triene-3β-ol | 1.6 | 0.5 | 0.03 |
| Zymosterol | 1.2 | 1.1 | 0.1 |
|  | 0.6 | 0.4 | 0.01 |
|  |  | 0.2 | 0.001 |
| 4β-Methylzymo- | 6.2 | 3.5 | 3.9 |
| sterol | 0.8 | 2.4 | 0.13 |
| 4,4-Dimethylcholest- | 0.8 | 12.8 | 0.03 |
| 8-ene-3β-ol |  |  |  |
| 4,4-Dimethylcholesta- | 2.25 | 0 | 3.0 |
| 8,14-dien-3β-ol |  |  |  |

Example 11

Test of meiosis inducing substances in the gonad test.

The gonad test was performed essentially as described by Byskov et al. *Mol. Reprod. Der.* 34, pp. 47–52 (1993). The results given in Table 6 were evaluated semiquantitatively as described by Westergaard et al. *Fertil. Steril.* 41, pp. 377–84 (1984).

TABLE 6

| Substance | Concentration, µg/ml | Result |
|---|---|---|
| 4,4-Dimethyl-zymosterol | 10 | ++ |
| 4,4-Dimethyl-5α-cholesta-8,14,24-triene-3β-ol | 30 | + |

We claim:

1. A method of regulating the meiosis in a mammalian germ cell, comprising administering ex vivo or in vitro of a compound formula I in an amount effective to regulate meiosis to a germ cell in need of such a treatment:

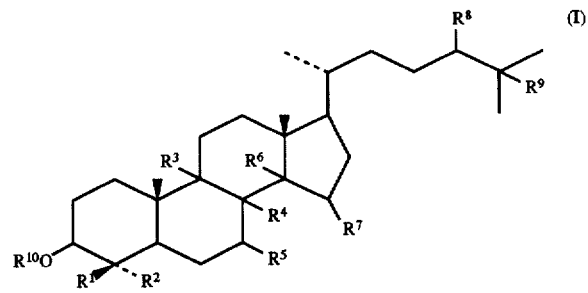

wherein $R^1$ and $R^2$, independently, are selected from the group comprising hydrogen, unbranched or branched $C_1$–$C_6$ alkyl which may be substituted by halogen or hydroxy or wherein $R^1$ and $R^2$ together with the carbon atom to which they are bound form a cyclopentane ting or a cyclohexane ring;

$R^3$ and $R^4$ together designate an additional bond between the carbon atoms to which they are bound in which case $R^5$ is hydrogen and $R^6$ and $R^7$ are either hydrogen or together they designate an additional double bond between the carbon atoms to which they are bound; or $R^5$ and $R^4$ together designate an additional bond between the carbon atoms to which they are bound in which case $R^3$ is hydrogen and $R^6$ and $R^7$ are either hydrogen or together they designate an additional bond between the carbon atoms to which they are bound; or $R^6$ and $R^4$ together designate an additional bond between the carbon atoms to which they are bound in which case $R^3$, $R^5$ and $R^7$ are all hydrogen;

$R^8$ and $R^9$ are hydrogen or together they designate an additional bond between the carbon atoms to which they are bound; and $R^{10}$ is either hydrogen or an acyl group or a group which together with the remaining part of the molecule forms an ether, for use as a medicament, wherein said mount is effective to regulate meiosis.

2. The method according to claim 1, wherein the germ cell is an oocyte.

3. The method according to claim 1, wherein the germ cell is a male germ cell.

4. The method of claim 1, wherein said compound is 4,4-dimethyl-5α-cholesta-8,14,24-triene-3β-ol.

5. The method of claim 1, wherein said compound is 4β-methylzymosterol.

* * * * *